(12) United States Patent
Klumpp et al.

(10) Patent No.: US 6,812,015 B1
(45) Date of Patent: Nov. 2, 2004

(54) HISTIDINE PROTEIN-PHOSPHATASE

(75) Inventors: Susanne Klumpp, Marburg (DE); Roland Kellner, Heppenheim (DE)

(73) Assignee: Merck Patent Gesellschaft, Darmstadt (DE)

(*) Notice: Subject to any disclaimer, the term of this patent is extended or adjusted under 35 U.S.C. 154(b) by 0 days.

(21) Appl. No.: 09/914,831

(22) PCT Filed: Mar. 2, 2000

(86) PCT No.: PCT/EP00/01774

§ 371 (c)(1),
(2), (4) Date: Sep. 4, 2001

(87) PCT Pub. No.: WO00/52175

PCT Pub. Date: Sep. 8, 2000

(30) Foreign Application Priority Data

Mar. 4, 1999 (DE) .......................................... 199 09 388

(51) Int. Cl.[7] .............................. C12N 9/14; C07K 16/00
(52) U.S. Cl. ..................................... 435/195; 530/387.1
(58) Field of Search ........................... 435/195, 252.33, 435/320.1; 536/23.2, 23.5; 530/387.1

(56) References Cited

FOREIGN PATENT DOCUMENTS

DE         19811194 A     9/1999

OTHER PUBLICATIONS

Hillier L. et al.: "zx64g11.r1 Soares__total__fetus Nb2HF8__9w__Homo sapiens cDNA clone" EMBL Database; Accession No. AA461149, Jun. 13, 1997.

Matthews Harry R. et al.: "Protein histidine phosphatase activity in rat liver and spinach leaves." FEBS Letters, vol. 364, No. 1, 1995, pp. 51–54.

Kim Younhee et al: "Removal of Phosphate from phosphohistidine in proteins." Bichimica et Biophysica Acta, vol. 1268, No. 2, 1995, pp. 221–228.

Ohmori Hitoshi et al.: "3–Phosphohistidine/6–Phospholysine Phosphatase from rat Brain as Acid Phosphatase" Journal of Biochemistry, vol. 116, No. 2, 1994, pp. 380–385.

Ostanin, Kirill et al: "Heterologous expression of human prostatic acid phosphatase and site–directed mutagenesis of the enzyme active site " J. Biol.Chem. (1994).

*Primary Examiner*—Nashaat T. Nashed
(74) *Attorney, Agent, or Firm*—Millen, White, Zelano & Branigan, P.C.

(57) ABSTRACT

The invention relates to a novel enzyme, histidine protein phosphatase, which is derived from mammalian sources, and its homologue variants. The invention further relates to DNA sequences encoding said proteins, to a process for preparing the latter, and to antibodies directed against them. The novel phosphatase can be used for diagnosis of pathological states of cell regulation and cell growth and as pharmaceutical drug which can be administered in conjunction with pathological disorders related to malfunctions of said enzyme.

9 Claims, 10 Drawing Sheets

```
GTGGACATCGACTCCGACGGCGTCTTCAAGTACGTGCTGATTCGAGTC
CACGCGGCGCCGCCCTCCGAAGCCCCGGGCGGCGAGAGCAAGGACATC
GTGCGTGGCTACAAGTGGGCCGAGTACCACGCCGACATCTACGACAAG
GTGTCGGGCGAGCTGCAGAAGAAGGGCCATGACTGCGAGTGCCTGGGC
GGCGGGCGCATCTCCCACCAGAGCCAGGACCGGAAGATCCACGTGTAC
GGCTACTCCATGGGCTACGGCGGGCCCAGCACTCCGTCTCCACCGAG
AAGATCAGAGCCAAGTACCCCGACTACGAGGTCACCTGG
```

FIG. 7a

```
AAAGLAQIPDVDIDSDGVFKYVLIRVHAAPPSEAPGGESKDIVRGYKW
AEYHADIYDKVSGELQKKGHDCECLGGGRISHQSQDRKIHVYGYSMGY
GRAQHSVSTEKIRAKYPDYEVTWADDGY
```

FIG. 7b

HISTIDINE PROTEIN-PHOSPHATASE

The invention relates to a novel enzyme, histidine protein phosphatase, which is derived from mammalian sources, and its homologue variants. The invention further relates to DNA sequences encoding said proteins, to a process for preparing the latter, and to antibodies directed against them. The novel phosphatase can be used for diagnosis of pathological states of cell regulation and cell growth and as pharmaceutical drug which can be administered in conjunction with pathological disorders related to malfunctions of said enzyme. In detail this invention relates to the application of said enzyme in diagnosis, treatment of disease, agonists and antagonists in identifying factors that function in histidine phosphorylation, as well as agonists and antagonists that are potentially useful in therapy.

BACKGROUND OF THE INVENTION

Protein phosphorylation is a fundamental biological process that often plays a key role in signal transduction and in the regulation of protein activity. Phosphorylation of serine, threonine, and tyrosine is common in eukaryotic signal transduction pathways. There is an extensive literature on biochemical methods for detection of phosphorylation of serine, threonine, and tyrosine on unknown proteins. For example, when mammalian cultured cells are treated with growth factors, cytokines, drugs, peptides, or other stimulatory molecules such as PDGF, NGF, IL-2, etc., phosphorylation of proteins at serine, threonine, and tyrosine can easily be detected by incubating the cells with radiolabeled phosphate, isolating proteins after treatment with a growth factor, etc., separating the proteins by SDS polyacrylamide gel electrophoresis, fixing the gel, and performing autoradiography to identify protein bands containing the labeled phosphate. Alternatively, proteins from treated and untreated cells can be separated using a two-dimensional system, and the position of protein spots can be compared. The apparent movement of a spot can indicate a change in modification state that results from a treatment. In another method, proteins are subject to acid hydrolysis to yield amino acids that can then be subjected to thin-layer chromatography and examined for the presence of radiolabeled phosphorus.

However, these protein chemistry methods employ conditions in which phosphorylated histidine, lysine, or arginine is unstable. In particular, phosphohistidine spontaneously breaks down with a half-life of about 5–100 minutes at low pH, but at neutral pH phosphohistidine has a half-life of days to weeks (Matthews, H. R. [1995] Pharmac. Ther. 67:323–350). For example, following electrophoresis, polyacrylamide gels for protein separation are generally fixed under acidic conditions. Similarly, the acidic conditions for amino acid hydrolysis also lead to breakdown of phosphohistidine.

Phosphorylated histidine has been demonstrated to play a key role in signal transduction in bacteria. Such pathways regulate many aspects of bacterial metabolism. For example, the ArcA/ArcB system governs aerobic and anaerobic metabolism in *E. coli* (luchi S, Weiner L. J Biochem (Tokyo) [1996] 120:1055–63). OmpR and OmpF govern the response to different osmotic conditions (Pratt L A, Hsing W, Gibson K E, Silhavy T J. Mol Microbiol [1996] 20:911–7). CheA and CheZ are involved in chemotaxis (Alon U. Nature [1999] 397:168–171). All of these proteins were first identified by genetic means: mutations in the corresponding genes cause phenotypes of interest, and the resulting proteins can be identified after cloning the relevant genes.

Similarly, it has recently been found that the eukaryotes *S. cerevisiae* and *Arabidopsis thaliana* have signal transduction systems with proteins that involve phosphorylation of histidine (Loomis et al., [1997] J. Cell Science 110:1141–1145). For example, the Sln1 protein has an extracellular sensor domain, a cytoplasmic histidine kinase domain, and an aspartate relay domain. ETR1 of the mustard plant *Arabidopsis thaliana* was also identified by mutants that fail to respond to ethylene. The ETR1 gene was then cloned and the protein studied, leading to the discovery that this protein is a histidine kinase. *S. cerevisiae* and *Arabidopsis thaliana* are genetically tractable organisms, and their proteins involved in histidine phosphorylation, such as Sln1 and Etr1, are usually identified by genetic means.

Existing techniques generally involve size separation of either proteins or phosphoamino acids.

Mammalian N-phosphorylation is important in energy metabolism and is altered in various types of cancer. For example, the Nm23 protein is a nucleoside diphosphate kinase that can use the ATP generated by glycolysis and oxidative phosphorylation to convert nucleoside and deoxynucleoside diphosphates into triphosphates. Nm23 becomes transiently phosphorylated on Histidine 118 as part of its ping-pong reaction mechanism. Nm23 is also capable of transferring its phosphate group onto histidine residues in ATP-citrate lyase and succinyl CoA synthetase. Thus, histidine phosphorylation plays an important role in energy metabolism in cells.

In humans there are several Nm23 proteins. In highly metastatic cancers, these Nm23 proteins are often expressed at low levels. Based on these results, Nm23 is thought to be an anti-oncogene. In addition, in certain cancers, mutations in particular Nm23 proteins are found. These mutations often affect the rate of phosphorylation or dephosphorylation of Nm23.

Taken together, these results indicate that N-phosphorylation plays an important role in energy metabolism and in cancer. Thus, proteins or drugs that modulate N-phosphorylation or dephosphorylation could be important in treatment of cancer or metabolic disorders such as obesity, anorexia, wasting due to cancer, HIV or other diseases, and so on. In addition, since N-phosphorylation plays a role in a wide variety of biological phenomena in other organisms, it may be that N-phosphorylation plays a role in other mammalian diseases and disorders, such as immune disorders, viral infection, genetic disorders, heart disease, and so on.

Unfortunately, mammals grow much more slowly than bacteria, *S. cerevisiae* and *Arabidopsis thaliana*, and it is therefore difficult to identify proteins involved in histidine, lysine, or arginine phosphorylation by the same genetic approaches used for these simpler organisms. In addition, biochemical techniques for identifying proteins that are phosphorylated on serine, threonine, and tyrosine are not generally applicable to identifying proteins that are phosphorylated on histidine, lysine, and arginine. There is therefore a need in the art for techniques and biochemical reagents for use in studying N-phosphorylation.

Histidine phosphatases and histidine kinases are enzymes acting in opposite directions. Histidine kinase effects the phosphorylation of certain histidine residues in proteins, whereas histidine phosphatases reverse this phosphorylation. Both enzymes probably play an important part in signal transduction, apoptosis, the control of cell growth and in cell differentiation. They are known to be diseases based on disturbances of these cellular functions. The present invention is thus based on the object of providing an agent which can be used to investigate the cause of the pathophysiological disturbances and, where appropriate, treat them.

Hormones or peptides stimulate cell surface receptors on a cell and induce cellular effects via a signal transduction pathway. Reversible phosphorylation of specific protein substrates by regulatory protein kinases and phosphatases plays an essential part in intracellular signal transmission. Receptor-bound, membrane-bound and intracellular protein kinases and phosphatases regulate the processes of cellular proliferation, cell differentiation and the immune system. Malfunctioning of these regulators or their activities is crucial for a large number of pathophysiological effects. Accordingly, protein kinases and phosphatases and the signal transduction pathway in which they are involved represent potential targets for the drug discovery process.

Signal transduction in mammals involves reversible phosphorylation of Ser/Thr/Tyr. Although histidine phosphate is known to be present in mammals (Crovello C S, Furie B C, Furie B (1995) Cell 82:279–286), it has not to date been possible to identify either the corresponding kinases or the relevant phosphatases. The difficulty is, inter alia, that histidine phosphate is unstable to hydrolysis and is not detected in standard phospho amino acid analysis.

The functions of His kinases and His phosphatases in bacteria have been investigated very thoroughly. Their involvement in chemotaxis and adaptation makes them promising points of attack for bacterial diseases.

SUMMARY OF THE INVENTION

The present invention relates to histidine protein phosphatase, in particular histidine protein phosphatase polypeptides and histidine protein phosphatase polynucleotides, recombinant materials and methods for their production. Such polypeptides and polynucleotides are of interest in relation to methods of treatment of certain diseases, including, but not limited to, cancer and metabolic disorders, cardiovascular diseases and diseases of the central nervous system, hereinafter referred to as "diseases of the invention". In a further aspect, the invention relates to methods for identifying agonists and antagonists (e.g., inhibitors) using the materials provided by the invention, and treating conditions associated with N-phosphorylation imbalance with the identified compounds. In a still further aspect, the invention relates to diagnostic assays for detecting diseases associated with inappropriate histidine protein phosphatase activity or levels.

The invention likewise includes corresponding variants and mutants, produced, for example, by random or controlled substitution, different splicing, deletion or addition of one or more nucleotides or amino acids, with the biological activity being essentially retained.

Thus, it is an object of the present invention to provide a polypeptide having the biological activity of a histidine phosphatase which has a high specificity for phosphohistidine and a molecular weight of 13.000–15.000, obtainable by purification from mammalian tissue by at least one anion exchange chromatography, one gel filtration and one affinity chromatograph step. Preferred mammalian tissue is derived from heart, kidney, liver, pancreas, skeletal muscle and testis. Preferred mammals are humans, rabbits, rats.

The polypeptide of the invention comprises at least the amino acid sequence motif (SEQ. No. 3) DCECLGGGRISHQSQD.

In another embodiment of the invention the polypeptide comprises at least the amino acid sequence motif (SEQ. No. 4)

DCECLGGGRISHQSQDX$^1$KIHVYGYSMX$^2$YGX$^3$AQH wherein X$^1$=K or R, X$^2$=A or G and X$^3$=P or R.

In a further embodiment of the invention the polypeptide comprises at least the amino acid sequence motif (SEQ. No. 5)

YHADIYDKVSGDMQKQGCDCECLGGGR-ISHQSQDKKIHVYGYSM.

All these partial sequences are highly conserved within the complete enzyme amino acid sequence and are deemed to be involved in the active site of said enzyme or have other biological or pharmaceutical relevance in mammals.

As a preferred embodiment of the invention the polypeptide has the biological activity of a histidine phosphatase which has a high specificity for phosphohistidine and a molecular weight of 13.000–15.000 and comprises the following amino acid sequence (SEQ. No. 2):

(M)AVADLALIPDVDIDSDGVFKYVLIRVHSAPRS
GAPAAESKEIVRGYKWAEYHADIYDKVS-
GDMQKQGGDGEGLGGGRISHQSQDKKIH-
VYGYSMAYGPAQHAISTEKIKAKYP-
DYEVTWANDGY

The methionine residue at the N-terminal of the sequence is not obligatory. The above indicated amino acid sequence is of human origin.

However, the invention discloses also especially homologue variants of said sequences. Therefore, it is a further object of the invention to provide a polypeptide having the biological activity of a histidine phosphatase which has a high specificity for phosphohistidine and a molecular weight of 13.000–15.000, the amino acid sequence of which has a homology of 64–99%, preferably 75–99%, compared with the sequence depicted above. As it is shown below the invention discloses a lot of other homologue polypeptides which all have the biological activity of a histidine protein phosphatase.

It is a further object of the invention to provide DNA sequences which code for a polypeptide indicated above and below. Especially, the invention relates to said DNA comprising the following nucleotide sequence (SEQ. No. 1):

(ATG)
GCGGTGGCGGACCTCGCTCTCATTCCT-
GATGTGGACATCGACTCCGACGGCGTCT-
TCAAGTATGTGCTGATCCGAGTCCACTCGGCT
CCCCGCTCCGGGGCTCCGGCTGCA-
GAGAGCAAGGAGATCGTGCGCGGCTA-
CAAGTGGGCTGAGTACCATGCGGACATC-
TACGACAAAGTGTCGGGCGACATGCAGAAGC
AAGGCTGCGACTGTGAGTGTCTGGGCG-
GCGGGCGCATCTCCCACCAGAGTCAGGA-
CAAGAAGATTCACGTGTACGGCTATTC-
CATGGCCTATGGTCCTGCCCAGCACGCCATTT
CAACTGAGAAAATCAAAGCCAAGTAC-
CCCGACTACGAGGTCACCTGGGCTAAC-
GACGGCTAC

The invention also relates to antibodies, preferably monoclonal antibodies, which are directed to the polypeptides according to this invention.

Finally, it is an object of the invention to provide a pharmaceutical preparation comprising a polypeptides defined above and below, where appropriate, together with suitable excipients, carriers and other active ingredients.

DETAILED DESCRIPTION

(A) Isolation and Purification

The histidine protein phosphatase was isolated from rabbit liver. The liver preparation starts from about 110 g of material cut into small pieces. It is mixed with homogenization buffer (220 ml of 30 mM triethanolamine/hydrochloric acid pH 7.5, 1 mM ethylenediaminetetraacetic acid, 300 mM sucrose, 0.1 mM benzamidine, 0.1% 2-mercaptoethanol) and comminuted in a homogenizer while cooling in ice. After a first centrifugation (10 min at 3800 g, 4° C.), the supernatant is recentrifuged (1 h at 48,000 g, 4° C.). This supernatant is filtered through gauze and frozen in aliquots of about 20 ml at −80° C.

Column Chromatographic Separation Methods

The histidine phosphatase was isolated by three purification steps (FIG. 1).

1. Anion Exchange Chromatography

The crude liver extract is centrifuged once again (30 min at 48,000 g). The supernatant is loaded onto a Source Q30 (Pharmacia, Freiburg) column equilibrated with buffer A (20 mM triethanolamine/hydrochloric acid pH 8.0, 1 mM ethylenediaminetetraacetic acid, 0.1% 2-mercaptoethanol, 0.02% sodium nitrite). Elution takes place with 200 mM sodium chloride in buffer A at a flow rate of 1 ml/min.

2. Gel Filtration

The active fraction (see activity determination) is stirred and cooled while solid ammonium sulfate is added (11.2 g to 17 ml). The pellet obtained by centrifugation (20 min at 48,000 g, 4° C.) is resuspended in buffer A and loaded onto a Superdex 75 26/60 1.6×60 cm (Pharmacia, Freiburg) column. The gel filtration takes place with the addition of 50 mM sodium chloride to buffer A at 1 ml/min.

3. Affinity Chromatography

The active fraction from the gel filtration is diluted in the ratio 1:3 with buffer B (20 mM triethanolamine/hydrochloric acid pH 8.0, 0.1 mM ethylenediaminetetraacetic acid, 0.1% 2-mercaptoethanol, 0.02% sodium nitrite) and adjusted to 10 mM in magnesium chloride. The sample is loaded onto a Blue Sepharose 6 25×510 mm (Pharmacia, Freiburg) column. Elution takes place using buffer B containing 200 mM sodium chloride at a flow rate of 1 ml/min.

(B) Specific Activity Detection

The activity of the soluble histidine phosphatase is determined from the dephosphorylation of $^{32}$P-labelled histidine-phosphorylated protein (CheA) as substrate. CheA is a recombinant bacterial histidine autokinase (Bilwes A M, Alex L A, Crane B R, Simon M I (1999) Cell 96:131–141); the C-terminal kinase domain phosphorylates the N-terminal His48. Free phosphate is produced in the reaction and is identified by thin-layer chromatography (polyethyleneimine cellulose plates, 0.5 M lithium chloride as mobile phase). Detection on the one hand via ammonium molybdate, and on the other hand by autoradiography (FIG. 2). There was no phosphate transfer to other proteins, nor was there any cleavage of the substrate into peptide fragments. The product is phosphate, i.e. a phosphohistidine protein phosphatase is involved.

The purified protein shows time-, temperature-, pH- and protein-dependent histidine dephosphorylation of the $^{32}$P-phosphorylated CheA (FIG. 3).

Stability

The purified protein shows storage stability in the crude homogenate and in the partially purified fractions.

Enzyme Assay

Substrate preparation: ($^{32}$P-labelling of CheA) Recombinant CheA (5 µl) is mixed with 0.5 µl of 100 mM phenylmethylsulfonyl fluoride in dimethyl sulfoxide and 5 µl of 500 mM HEPES pH 8.0, 1 mM magnesium chloride. Addition of 108 µCurie of $^{32}$P-g-adenosine triphosphate, 5 µl of 10 µM adenosine triphosphate and 50 µl of water is followed by incubation at 37° C. for 3 h.

Activity Determination

The substrate (10 µl of $^{32}$P-CheA) is mixed with 10 µM of assay buffer (100 mM triethanolamine/hydrochloric acid pH 8.0, 0.1% 2-mercaptoethanol, 0.02% sodium nitrite) and the enzyme solution. The reaction takes place at 37° C. in 30 min. Then 2 µl of 500 mM ethylenediaminetetraacetic acid and 126 µl of 1:1 methanol/acetone are added. After a centrifugation (5 min at 15,800 g), the supernatant is removed and measured in a scintillation counter.

The described phosphatase is thus differentiated from other protein phosphatases on the basis of 1) the specificity for phosphohistidine (Table 1), the histidine phosphatase did not hydrolyze e.g. p-nitrophenyl phosphate;
2) the activity not being inhibited by okadaic acid or vanadate (Table 2);
3) the molecular weight being considerably smaller.

TABLE 1

| Hydrolysis by the novel histidin protein phosphatase | |
| --- | --- |
| Azocoll | − |
| [γ-$^{32}$P] ATP | − |
| p-nitrophenyl phosphate | − |
| [γ-$^{32}$P] Ser/Thr-Casein | − |
| Tyr-xxx | − |
| [γ-$^{32}$P] His-nucleoside diphosphate kinase | − |
| [γ-$^{32}$P] His-cheA | + |

TABLE 2

| Reagents affecting histidine phosphatase activities. | | |
| --- | --- | --- |
| Reagent | Concentration | Activity (%) |
| Phosphate | 10 mM | 0 |
| Okadaic acid | 10 µM | 108 |
| Microcystin | 5 nM | 110 |
| Tautomycin | 0.5 nM | 90 |
| Inhibitor protein I$_1$ | 1 nM | 120 |
| Molybdate | 10 µM | 71 |
| Vanadate | 10 µM | 62 |
| Fluoride | 5 mM | 105 |
| EDTA | 5 mM | 108 |
| EGTA | 5 mM | 91 |
| Mg$^{2+}$ | 1 mM | 142 |
| Mg$^{2+}$ | 10 mM | 226 |
| Ca$^{2+}$ | 1 mM | 165 |
| Ca$^{2+}$ | 10 mM | 240 |

100% = xxx nmol/min × mg$^{-1}$ (C) Characterization of the Histidine Protein Phosphatase The purified protein fraction contained a defined band with an apparent molecular weight of 14.000 according to analysis by SDS gel electrophoresis (FIG. 4). Mass analysis identified a molecular weight of the protein of 13.768 (FIG. 5). The histidine protein phosphatase is N-terminally blocked by an acetyl group. Sequence information is therefore not accessible by Edman degradation and for protein characterization a proteolytic cleavage is required.

(D) Protein Analytical Determination

The active fraction (FIG. 4) underwent enzymatic cleavage to determine the amino acid sequence, and the resulting peptide fragments were sequenced by Edman degradation and mass spectrometry applying standard techniques as described in the literature (Kellner R, Lottspeich F, Meyer H E (1999) Microcharacterization of Proteins, Wiley-VCH).

Enzymatic Fragmentation

The gel band was cut out using a scalpel and transferred into an Eppendorf tube. The enzymatic fragmentation took place after addition of trypsin as protease (1 µg of trypsin, 100 µl of 0.5 M ammonium bicarbonate, 37° C., 12 h). The resulting peptide fragments were extracted (50% trifluoroacetic acid, 50% acetonitrile). The extract was concentrated in a vacuum centrifuge.

Chromatographic Separation of the Peptide Fragments

The peptide fragments were dissolved in eluent A (0.1% trifluoroacetic acid in water) and applied for separation by reversed phase chromatography (eluent B: 20% 0.1% trifluoroacetic acid in water, 80% acetonitrile). After fractionation based on UV determination at 214 nm (see FIG. 6), the separated peptide fragments were in dissolved form and were determined by Edman sequencing and mass spectrometry.

Edman Sequencing and Mass Spectrometric Determinations

The liquid fractions after the chromatographic separation were 90% employed for Edman sequencing (standard conditions, apparatus: model 494, PE-Applied Biosystems, Weiterstadt). The remaining part of the fraction was employed for a mass analysis (MALDI-MS), (apparatus: Voyager STR, Perseptive Biosystems, Wiesbaden).

Identified Peptide Sequences

The following peptide sequences were determined (rabbit):

AAAGLAQIPD VDIDSDGVFK (positions 1–20 of SEQ ID NO:6)
YVLIR (positions 21–25 of SEQ ID NO:6)
VHAAPPSEAPGGESK (positions 26–40 of SEQ ID NO:6)
DIVR (positions 41–44 of SEQ ID NO:6)
WAEYHADIYDK (positions 48–58 of SEQ ID NO:6)
VSGELQK (positions 59–65 of SEQ ID NO:6)
ISHQSQDR (positions 78–85 of SEQ ID NO:6)
KIHVYGSMGYGR (positions 86–98 of SEQ ID NO:6)
YPDYEVTWADDGY (positions 112–124 of SEQ ID NO:6)

These peptides lead to the enzyme peptide from rabbit (SEQ No. 6):

AAAGLAQIPDVDIDSDGVFKYV-
LIRVHAAPPSEAPGGESKDIVRGYK-
WAEYHADIYDKVSGELQKKGHDCECLGG-
GRISHQSQDRKIHVYGYSMGYGRAQHSVSTE
KIRAKYPDYEVTWADDGY (E) Nucleotide Sequencing A rabbit DNA library was screened with primers selected from the achieved amino acid sequence for the histidine protein phosphatasenucleotide sequence. Cloning and sequencing identified the nucleotide sequence given in FIG. 7a.

The 327 bases translate for the histidine protein phosphataseprotein sequence beginning at position 11 to 119 (FIG. 7b).

Data Base Analysis

A database search was carried out using the BLAST algorhythm. Homologous proteins could be identified from *C.elegans, Drosophila melanogaster, Drosophila pseudoobscura* in protein databases.

In nucleotide databases ESTs were identified in human, rat and mouse. A human homologue has not not been published yet. According to these EST assemblies human histidine protein phosphatase protein was found to have the following sequence (SEQ. No 2 without a methionine residue):

AVADLALIPDVDIDSDGVFKYVLIRVH-
SAPRSGAPAAESKEIVRGYKWAEYHAD-
IYDKVSGDMQKQGCDECLGGGR-
ISHQSQDKKIHVYGYSMAYGPAQHAISTEKIKA
KYPDYEVTWANDGY

A rat homologue has not been published yet. According to these EST assemblies rat histidine protein phosphatase protein was found to have the following sequence (SEQ. No. 7):

NGLNTTRGKGSSPLGKDHQELELLTPY-
PAVKFSVGPTRATRAYPEATLPTSADIY-
DKVSGELQKNGYDCECLGGGR-
ISHQSQDRKIHVYGYSMGYGRAQHSVSTEKIKA
KYPDYEVTWADDGY

A mouse homologue has not been published yet. According to these EST assemblies mouse histidine protein phosphatase protein was found to have the following sequence (SEQ. No. 8):

MAADLGQIPDVDIDSDGVFKYV-
LIRVHLAEPSGDPAKECKEIVRGYK-
WAEYHADIYDKVSGELQRNGYDCECLGG-
GRISHQSQDRKIHVYGYSMGYGRAQHSVSTEK
IKAKYPDYEVTWADDGY

TABLE 3

Sequence homology for the protein histidine phosphatase from various species given in % identity.

|  | 1 | 2 | 3 | 4 | 5 | 6 | 7 |
|---|---|---|---|---|---|---|---|
| 1 human | 100 | 84.0 | 65.3 | 64.3 | 68.2 | 38.0 | 40.3 |
| 2 rabbit |  | 100 | 72.4 | 71.4 | 71.0 | 36.0 | 42.0 |
| 3 mouse |  |  | 100 | 67.3 | 52.7 | 32.7 | 33.3 |
| 4 rat |  |  |  | 100 | 51.6 | 30.8 | 29.5 |
| 5 zebra fish |  |  |  |  | 100 | 33.7 | 42.1 |
| 6 c. elegans |  |  |  |  |  | 100 | 39.7 |
| 7 drosophila |  |  |  |  |  |  | 100 |

(E) Protein Localization and Tissue Distribution

The human histidine protein phosphatase gene is localized at chromosome 9 (9 q33-Tel, marker sts-N90764, interval D9S159-qTEL).

Sources for the expression of cDNAs were used:

Brain, breast, CNS, colon, foreskin, germ cell, heart, kidney, liver, lung, muscle, pancreas, parathyroid, pooled, prostate, spleen, testis, thyroid, tonsil, uterus, whole embryo.

Analyzing the distribution of histidine protein phosphatasemRNA showed an increased level in normal tissues as heart, kidney, liver, pancreas, skeletal muscle and testis (FIGS. 8a–8c).

(F) Anti-histidine Phosphatase Antibodies

Anti-Histidine phosphatase antibodies were generated against three distinct regions of the protein, namely the n-terminal, the middle and the c-terminal part of the molecule. For this puropose three peptide sequences were chosen:

peptide 1—QIPDVDIDSD GVFKYV (16aa, SEQ. No. 9);
peptide 2—CLGGGRISHQ SQDK (14aa, SEQ. No. 10);
peptide 3—CTEKIKAKYP DYEV (14aa, SEQ. No. 11).

The peptides were synthesized using standard FMOC-chemistry. For immunization the peptides were injected (4 injections) each into two rabbits and four blood samples were taken. Final bleeding was taken after ca. 3 month. The generated antibodies are useful for detection and localization of the histidine phosphatase.

Furthermore, the different regions within the molecule can be analyzed individually. Especially the highly conserved central part of the histidine phosphatase containing the following amino acid sequence:

DCECLGGGRISHQSQD (SEQ. No. 3)

is assumed to contain the active site responsible for the proteins function in vivo. The anti-peptide antibody against this region is for inhibitory or neutralizing use.

The characteristics of the histidine protein phosphatase can be summarized as follows:

1. The amino acid sequence of human histidine protein phosphatase comprises about 124 amino acids.
2. The amino acid sequence of the histidine protein phosphatase is highly homologous in the C-terminal part but only weak homology is given for the N-terminal part.
3. The molecular weight is 13.800 +/−100 (FIG. 5).
4. The histidine protein phosphatase is N-terminal blocked by an acetylation.

Pharmaceutical Preparations

The native as well as the recombinant protein(s) may be used as a medicament which can be applied to patients directly or within pharmaceutical compositions. Thus, it is a further aspect of this invention to provide a recombinant or native protein as defined above and below applicable as a medicament and a respective pharmaceutical composition comprising said protein and a pharmaceutically acceptable diluent, carrier or excipient therefor.

The pharmaceutical compositions of the invention may contain additionally further active pharmaceutical compounds of a high diversity.

As used herein, the term "pharmaceutically acceptable carrier" means an inert, non toxic solid or liquid filler, diluent or encapsulating material, not reacting adversely with the active compound or with the patient. Suitable, preferably liquid carriers are well known in the art such as sterile water, saline, aqueous dextrose, sugar solutions, ethanol, glycols and oils, including those of petroleum, animal, vegetable, or synthetic origin, for example, peanut oil, soybean oil and mineral oil.

The formulations according to the invention may be administered as unit doses containing conventional non-toxic pharmaceutically acceptable carriers, diluents, adjuvants and vehicles which are typical for parenteral administration.

The term "parenteral" includes herein subcutaneous, intravenous, intra-articular and intratracheal injection and infusion techniques. Also other administrations such as oral administration and topical application are suitable. Parenteral compositions and combinations are most preferably adminstered intravenously either in a bolus form or as a constant fusion according to known procedures. Tablets and capsules for oral administration contain conventional excipients such as binding agents, fillers, diluents, tableting agents, lubricants, disintegrants, and wetting agents. The tablets may be coated according to methods well known in the art. Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives like suspending agents, emulsifying agents, non-aqueous vehicles and preservatives. Topical applications may be in the form of aqueous or oily suspensions, solutions, emulsions, jellies or preferably emulsion ointments.

Unit doses according to the invention may contain daily required amounts of the protein according to the invention, or sub-multiples thereof to make up the desired dose. The optimum therapeutically acceptable dosage and dose rate for a given patient (mammals, including humans) depends on a variety of factors, such as the activity of the specific active material employed, the age, body weight, general health, sex, diet, time and route of administration, rate of clearance, enzyme activity (units/mg protein), the object of the treatment, i. e., therapy or prophylaxis and the nature of the disease to be treated.

Therefore, in compositions and combinations in a treated patient (in vivo) a pharmaceutical effective daily dose of the protein of this invention is between about 0.01 and 100 mg/kg body weight (based on a specific activity of 100 kU/mg), preferably between 0.1 and 10 mg/kg body weight. According to the application form one single dose may contain between 0.5 and 10 mg of histidin protein phosphatase.

BRIEF DESCRIPTION OF THE FIGURES

FIG. 7a: (partial) Nucleotide sequence of rabbit histidine protein phosphatase FIG. 7b: translated complete amino acid sequence of rabbit histidine protein phosphatase

SEQUENCE LISTING

<160> NUMBER OF SEQ ID NOS: 11

Figure 1:
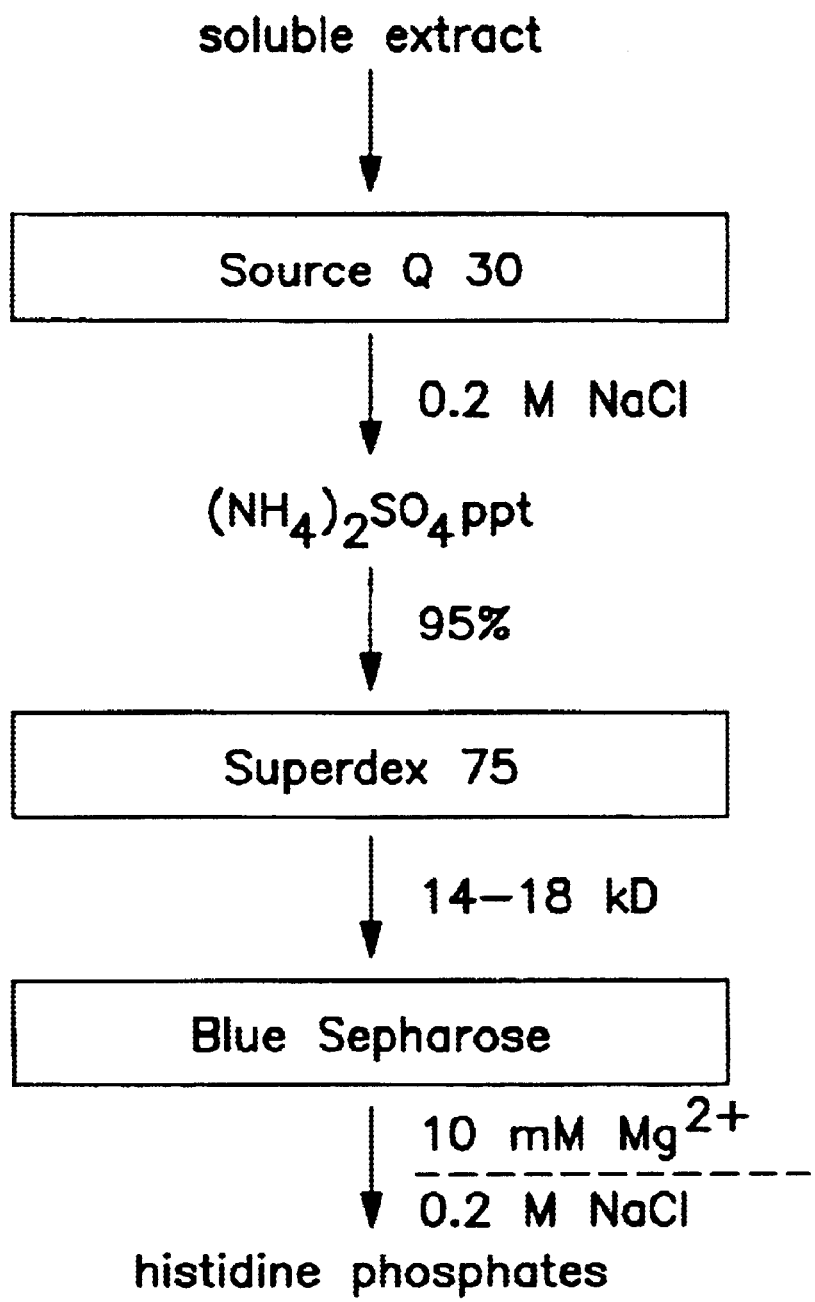
FIG. 1: Purification scheme used for the isolation of the histidine phosphatase
Figure 2:
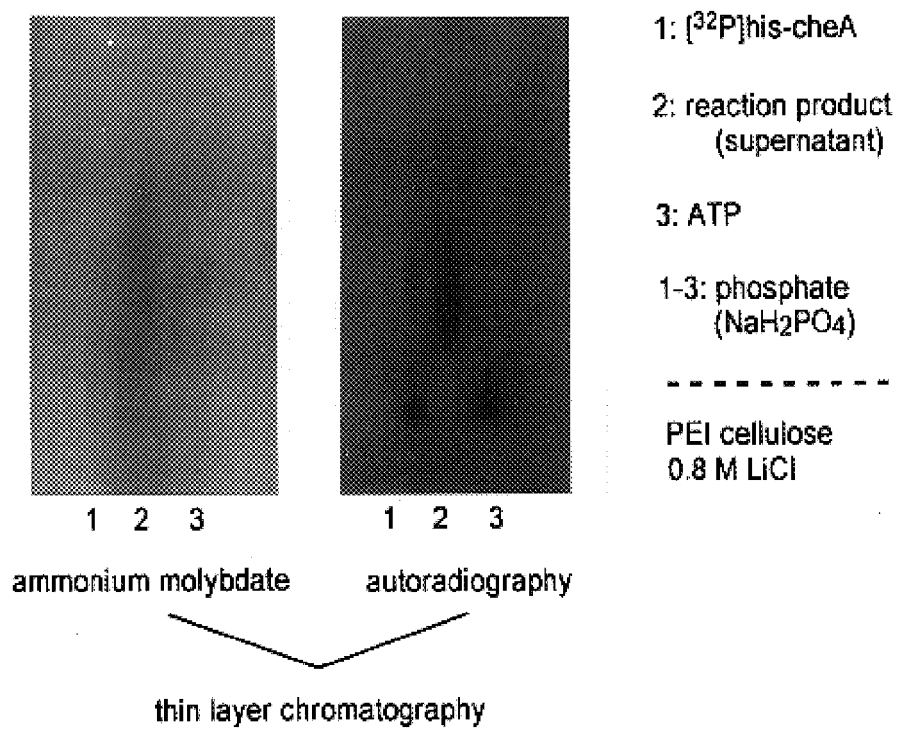
FIG. 2: Identification of inorganic phosphate as reaction product of histidine phosphatase cleavage. The plates show thin layer chromatography (PEI cellulose, 0.8 M LiCl); left panel: ammonium molybdate treatment; right panel: autoradiography treatment; 1: [$^{32}$P]his-cheA, 2: reaction product, 3: ATP, 1–3: phosphate (NaH2PO4)
Figure 3:
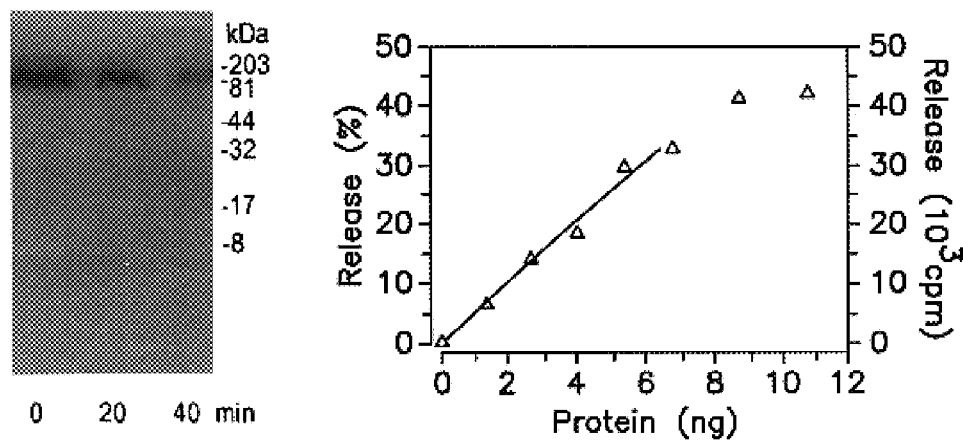
FIG. 3: Time and protein dependent dephosphorylation of the substrate cheA; left panel: degradation after 0, 20 and 40 min, right panel: release of radio labeled phosphate (left y-axis: %, right y-axis: radio activity) of different amounts of substrate (x-axis: ng protein).
Figure 4:
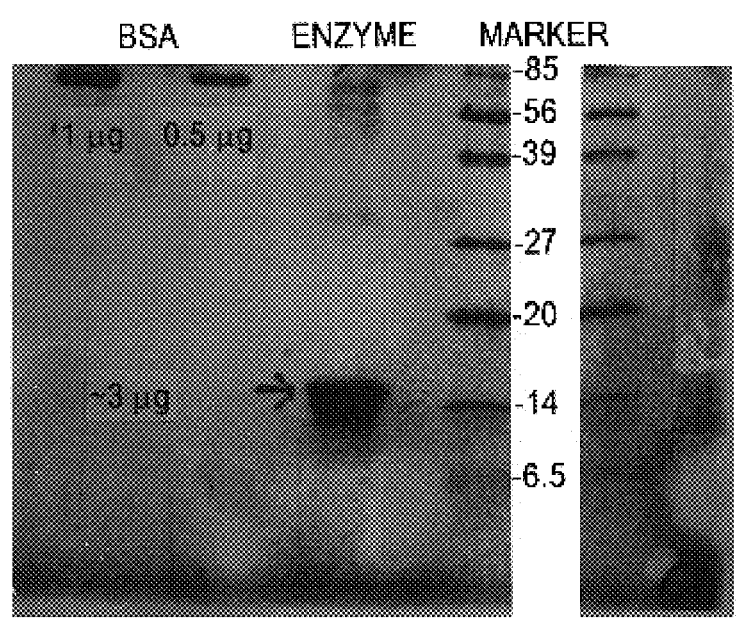
FIG. 4: Analysis of the fraction with active histidine phosphatase (SDS-PAGE); AF: active fraction; 1,2: BSA (1 µg, 0.5 µg), 3: AF; 4,5: molecular markers.
Figure 5:
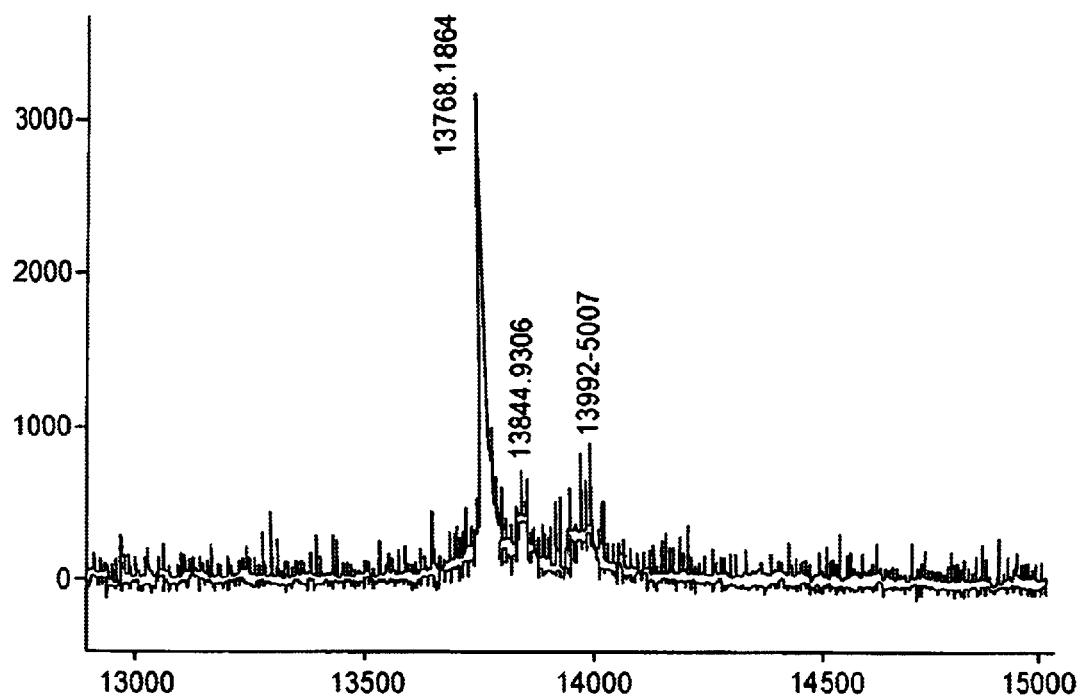
FIG. 5: Mass analysis of the histidine phosphatase. Y-axis: cunts, x-axis: mass(m/z)
Figure 6:
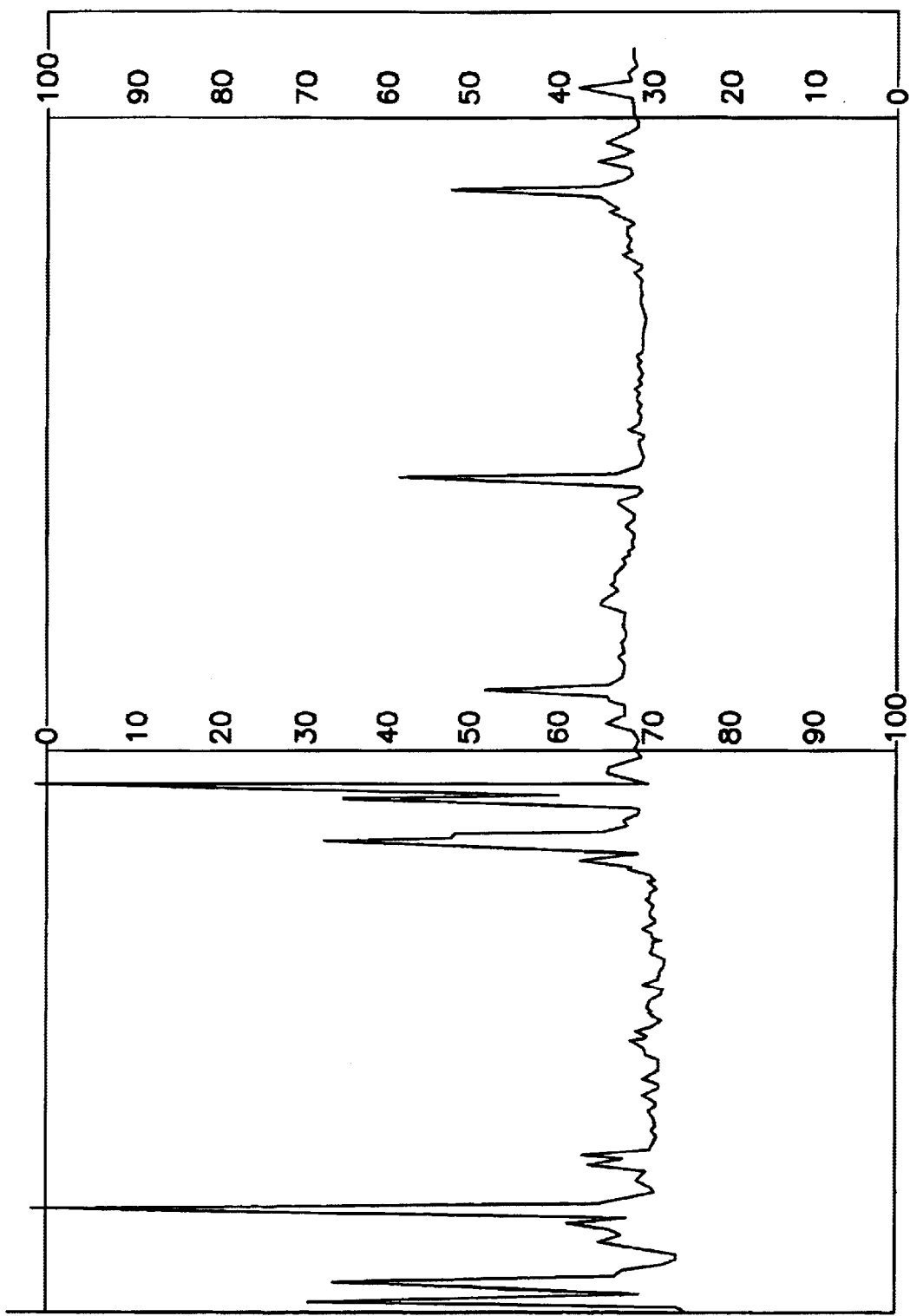
FIG. 6: Reversed phase chromatographic separation of histidine phosphatase after enzymatic fragmentation; eluent A: 0. 1% trifluoroacetic acid in water and eluent B: 20% 0.1% trifluoroacetic acid in water, 80% acetonitrile; UV determination at 214 nm
Figure 8A:
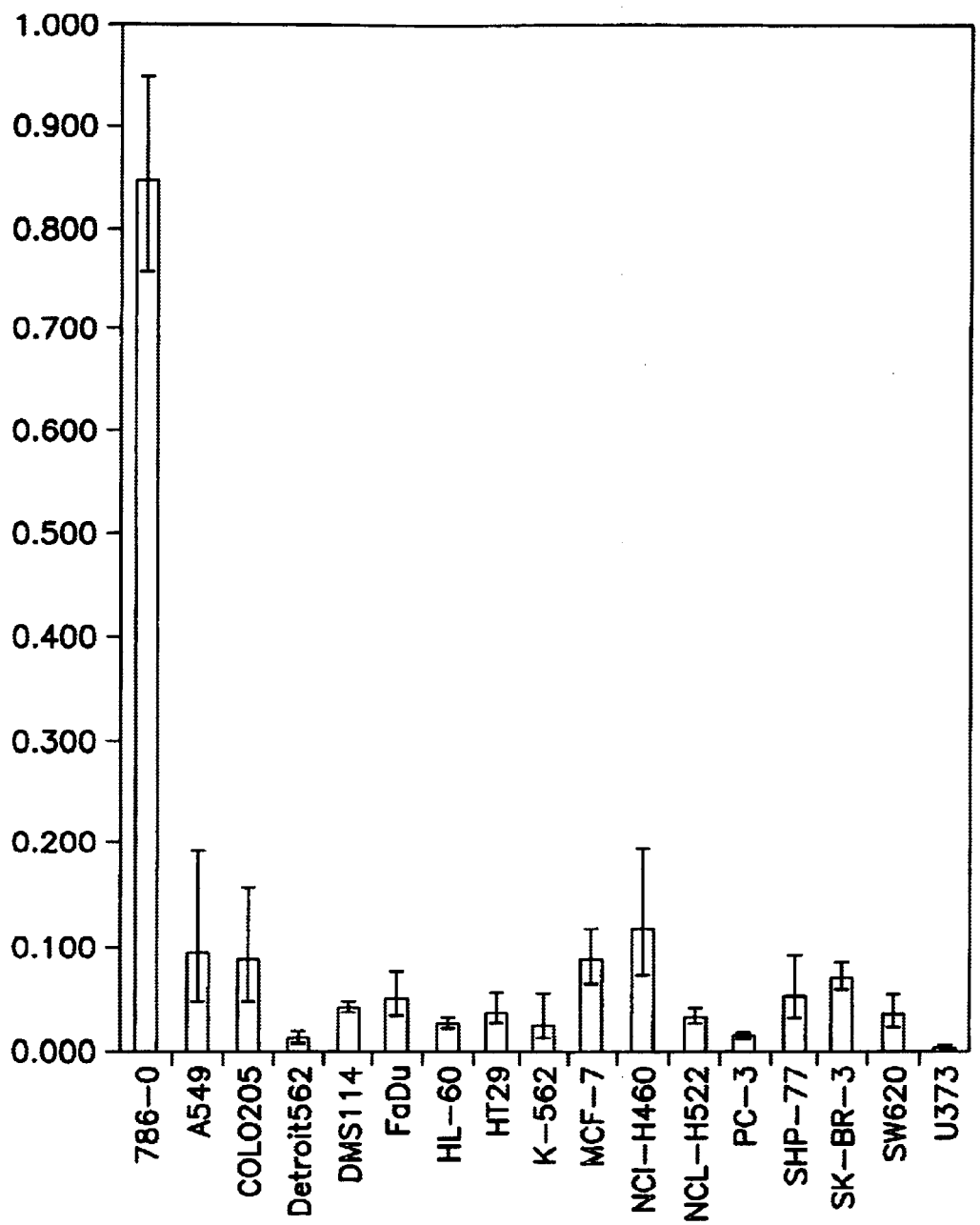
FIG. 8a: Tumor cell line distribution of histidine protein phosphatase FIG. 8b. Tissue distribution of histidine protein phosphatase in tumor tissue.
Figure 8B:
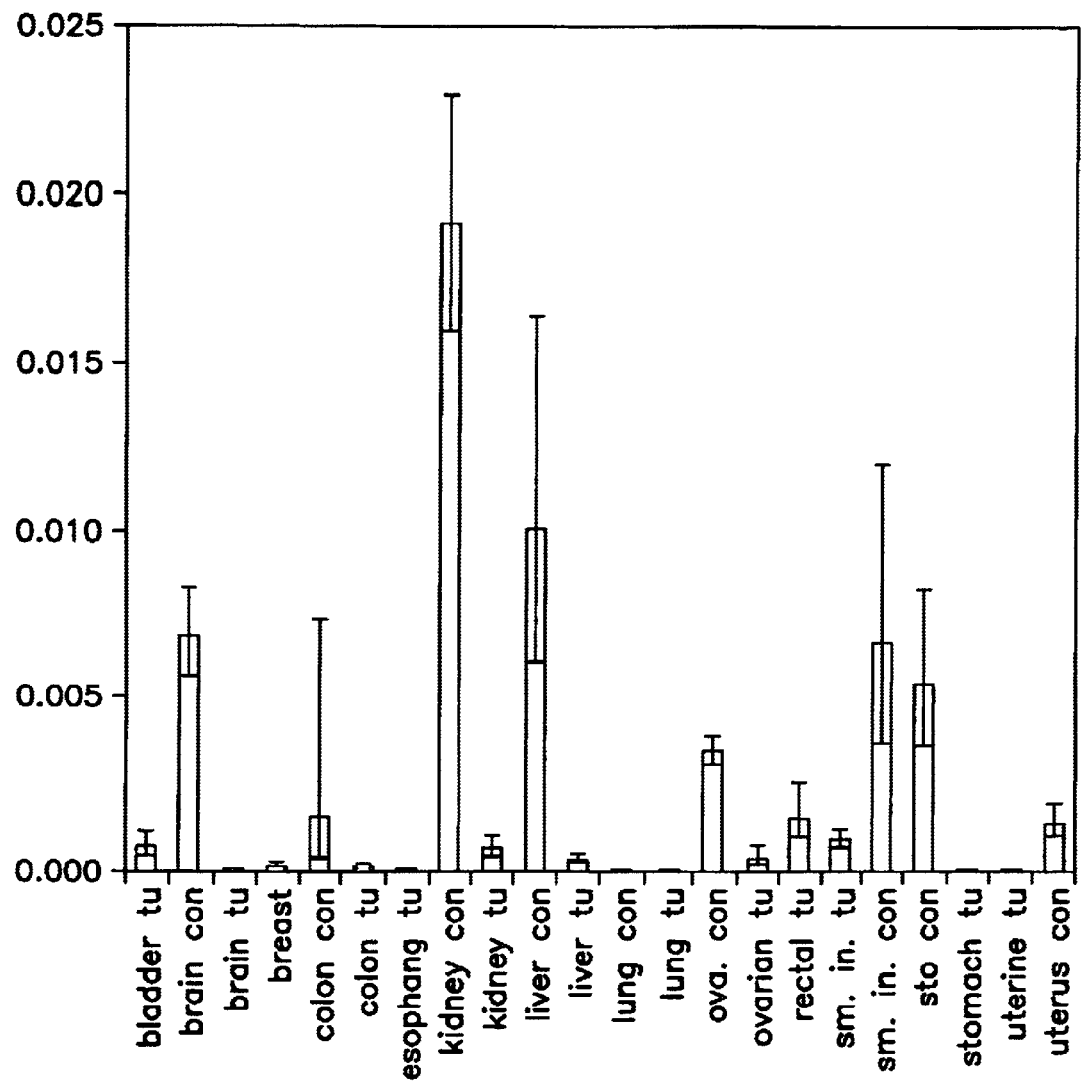
FIG. 8c. Tissue distribution of histidine phosphatase in normal tissue.
Figure 8C:
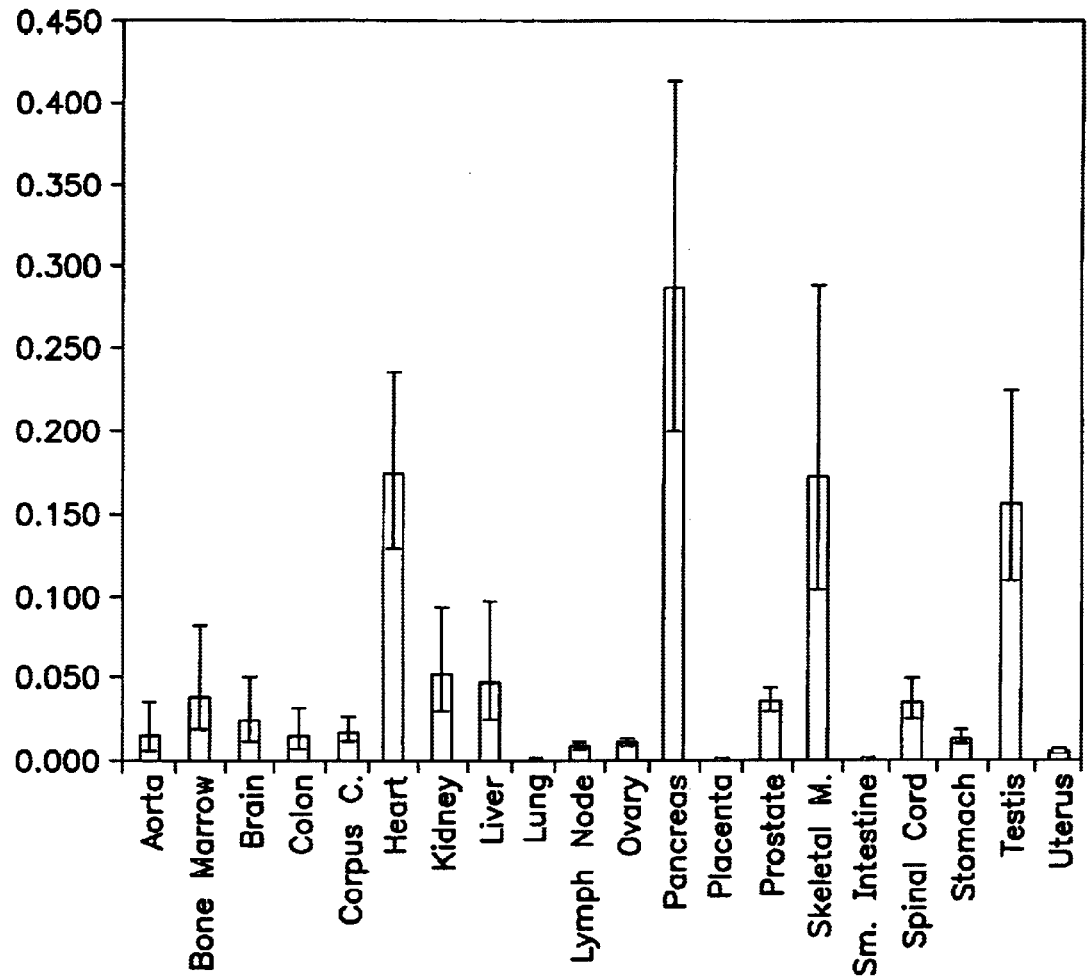

<210> SEQ ID NO 1
<211> LENGTH: 375
<212> TYPE: DNA
<213> ORGANISM: Homo sapiens
<220> FEATURE:
<221> NAME/KEY: CDS
<222> LOCATION: (1)..(375)
<223> OTHER INFORMATION: Human histidine protein phosphatase

<400> SEQUENCE: 1

| | | | | | | | | | | | | | | | | |
|---|---|---|---|---|---|---|---|---|---|---|---|---|---|---|---|---|
| atg | gcg | gtg | gcg | gac | ctc | gct | ctc | att | cct | gat | gtg | gac | atc | gac | tcc | 48 |
| Met | Ala | Val | Ala | Asp | Leu | Ala | Leu | Ile | Pro | Asp | Val | Asp | Ile | Asp | Ser | |
| 1 | | | | 5 | | | | | 10 | | | | | 15 | | |
| gac | ggc | gtc | ttc | aag | tat | gtg | ctg | atc | cga | gtc | cac | tcg | gct | ccc | cgc | 96 |
| Asp | Gly | Val | Phe | Lys | Tyr | Val | Leu | Ile | Arg | Val | His | Ser | Ala | Pro | Arg | |
| | | | 20 | | | | | 25 | | | | | 30 | | | |
| tcc | ggg | gct | ccg | gct | gca | gag | agc | aag | gag | atc | gtg | cgc | ggc | tac | aag | 144 |
| Ser | Gly | Ala | Pro | Ala | Ala | Glu | Ser | Lys | Glu | Ile | Val | Arg | Gly | Tyr | Lys | |
| | 35 | | | | | 40 | | | | | 45 | | | | | |
| tgg | gct | gag | tac | cat | gcg | gac | atc | tac | gac | aaa | gtg | tcg | ggc | gac | atg | 192 |
| Trp | Ala | Glu | Tyr | His | Ala | Asp | Ile | Tyr | Asp | Lys | Val | Ser | Gly | Asp | Met | |
| 50 | | | | | 55 | | | | | 60 | | | | | | |
| cag | aag | caa | ggc | tgc | gac | tgt | gag | tgt | ctg | ggc | ggc | ggg | cgc | atc | tcc | 240 |
| Gln | Lys | Gln | Gly | Cys | Asp | Cys | Glu | Cys | Leu | Gly | Gly | Gly | Arg | Ile | Ser | |
| 65 | | | | 70 | | | | | 75 | | | | | 80 | | |
| cac | cag | agt | cag | gac | aag | aag | att | cac | gtg | tac | ggc | tat | tcc | atg | gcc | 288 |
| His | Gln | Ser | Gln | Asp | Lys | Lys | Ile | His | Val | Tyr | Gly | Tyr | Ser | Met | Ala | |
| | | | 85 | | | | | 90 | | | | | 95 | | | |
| tat | ggt | cct | gcc | cag | cac | gcc | att | tca | act | gag | aaa | atc | aaa | gcc | aag | 336 |
| Tyr | Gly | Pro | Ala | Gln | His | Ala | Ile | Ser | Thr | Glu | Lys | Ile | Lys | Ala | Lys | |
| | | 100 | | | | | 105 | | | | | 110 | | | | |
| tac | ccc | gac | tac | gag | gtc | acc | tgg | gct | aac | gac | ggc | tac | | | | 375 |
| Tyr | Pro | Asp | Tyr | Glu | Val | Thr | Trp | Ala | Asn | Asp | Gly | Tyr | | | | |
| 115 | | | | | 120 | | | | | 125 | | | | | | |

<210> SEQ ID NO 2
<211> LENGTH: 125
<212> TYPE: PRT
<213> ORGANISM: Homo sapiens

<400> SEQUENCE: 2

Met Ala Val Ala Asp Leu Ala Leu Ile Pro Asp Val Asp Ile Asp Ser
1               5                   10                  15

Asp Gly Val Phe Lys Tyr Val Leu Ile Arg Val His Ser Ala Pro Arg
            20                  25                  30

Ser Gly Ala Pro Ala Ala Glu Ser Lys Glu Ile Val Arg Gly Tyr Lys
        35                  40                  45

Trp Ala Glu Tyr His Ala Asp Ile Tyr Asp Lys Val Ser Gly Asp Met
    50                  55                  60

Gln Lys Gln Gly Cys Asp Cys Glu Cys Leu Gly Gly Gly Arg Ile Ser
65                  70                  75                  80

His Gln Ser Gln Asp Lys Lys Ile His Val Tyr Gly Tyr Ser Met Ala
                85                  90                  95

Tyr Gly Pro Ala Gln His Ala Ile Ser Thr Glu Lys Ile Lys Ala Lys
            100                 105                 110

Tyr Pro Asp Tyr Glu Val Thr Trp Ala Asn Asp Gly Tyr
        115                 120                 125

```
<210> SEQ ID NO 3
<211> LENGTH: 16
<212> TYPE: PRT
<213> ORGANISM: mammalian
<220> FEATURE:
<221> NAME/KEY: PEPTIDE
<222> LOCATION: (1)..(16)
<223> OTHER INFORMATION: conserved mammalian sequence

<400> SEQUENCE: 3

Asp Cys Glu Cys Leu Gly Gly Gly Arg Ile Ser His Gln Ser Gln Asp
 1               5                  10                  15

<210> SEQ ID NO 4
<211> LENGTH: 33
<212> TYPE: PRT
<213> ORGANISM: mammalian
<220> FEATURE:
<221> NAME/KEY: PEPTIDE
<222> LOCATION: (1)..(33)
<223> OTHER INFORMATION: conserved mammalian sequence 2
<221> NAME/KEY: SITE
<222> LOCATION: (17)
<223> OTHER INFORMATION: X =  K or R
<221> NAME/KEY: SITE
<222> LOCATION: (27)
<223> OTHER INFORMATION: X = A or G
<221> NAME/KEY: SITE
<222> LOCATION: (30)
<223> OTHER INFORMATION: X = P or R

<400> SEQUENCE: 4

Asp Cys Glu Cys Leu Gly Gly Gly Arg Ile Ser His Gln Ser Gln Asp
 1               5                  10                  15

Xaa Lys Ile His Val Tyr Gly Tyr Ser Met Xaa Tyr Gly Xaa Ala Gln
                20                  25                  30

His

<210> SEQ ID NO 5
<211> LENGTH: 44
<212> TYPE: PRT
<213> ORGANISM: mammalian
<220> FEATURE:
<221> NAME/KEY: PEPTIDE
<222> LOCATION: (1)..(44)
<223> OTHER INFORMATION: conserverd mammalian sequence 3

<400> SEQUENCE: 5

Tyr His Ala Asp Ile Tyr Asp Lys Val Ser Gly Asp Met Gln Lys Gln
 1               5                  10                  15

Gly Cys Asp Cys Glu Cys Leu Gly Gly Gly Arg Ile Ser His Gln Ser
                20                  25                  30

Gln Asp Lys Lys Ile His Val Tyr Gly Tyr Ser Met
            35                  40

<210> SEQ ID NO 6
<211> LENGTH: 124
<212> TYPE: PRT
<213> ORGANISM: rabbit
<220> FEATURE:
<221> NAME/KEY: PEPTIDE
<222> LOCATION: (1)..(124)
<223> OTHER INFORMATION: rabbit histidine protein phosphatase

<400> SEQUENCE: 6

Ala Ala Ala Gly Leu Ala Gln Ile Pro Asp Val Asp Ile Asp Ser Asp
```

```
                 1               5                  10                  15
Gly Val Phe Lys Tyr Val Leu Ile Arg Val His Ala Pro Pro Ser
                20                  25                  30

Glu Ala Pro Gly Gly Glu Ser Lys Asp Ile Val Arg Gly Tyr Lys Trp
                35                  40                  45

Ala Glu Tyr His Ala Asp Ile Tyr Asp Lys Val Ser Gly Glu Leu Gln
                50                  55                  60

Lys Lys Gly His Asp Cys Glu Cys Leu Gly Gly Arg Ile Ser His
 65                  70                  75                  80

Gln Ser Gln Asp Arg Lys Ile His Val Tyr Gly Tyr Ser Met Gly Tyr
                85                  90                  95

Gly Arg Ala Gln His Ser Val Ser Thr Glu Lys Ile Arg Ala Lys Tyr
                100                 105                 110

Pro Asp Tyr Glu Val Thr Trp Ala Asp Asp Gly Tyr
                115                 120
```

<210> SEQ ID NO 7
<211> LENGTH: 123
<212> TYPE: PRT
<213> ORGANISM: rat
<220> FEATURE:
<221> NAME/KEY: PEPTIDE
<222> LOCATION: (1)..(123)
<223> OTHER INFORMATION: rat histidine protein phosphatase

<400> SEQUENCE: 7

```
Asn Gly Leu Asn Thr Thr Arg Gly Lys Gly Ser Ser Pro Leu Gly Lys
 1               5                  10                  15

Asp His Gln Glu Leu Glu Leu Leu Thr Pro Tyr Pro Ala Val Lys Phe
                20                  25                  30

Ser Val Gly Pro Thr Arg Ala Thr Arg Ala Tyr Pro Glu Ala Thr Leu
                35                  40                  45

Pro Thr Ser Ala Asp Ile Tyr Asp Lys Val Ser Gly Glu Leu Gln Lys
                50                  55                  60

Asn Gly Tyr Asp Cys Glu Cys Leu Gly Gly Arg Ile Ser His Gln
 65                  70                  75                  80

Ser Gln Asp Arg Lys Ile His Val Tyr Gly Tyr Ser Met Gly Tyr Gly
                85                  90                  95

Arg Ala Gln His Ser Val Ser Thr Glu Lys Ile Lys Ala Lys Tyr Pro
                100                 105                 110

Asp Tyr Glu Val Thr Trp Ala Asp Asp Gly Tyr
                115                 120
```

<210> SEQ ID NO 8
<211> LENGTH: 124
<212> TYPE: PRT
<213> ORGANISM: mouse
<220> FEATURE:
<221> NAME/KEY: PEPTIDE
<222> LOCATION: (1)..(124)
<223> OTHER INFORMATION: mouse histidine protein phosphatase

<400> SEQUENCE: 8

```
Met Ala Ala Asp Leu Gly Gln Ile Pro Asp Val Asp Ile Asp Ser Asp
 1               5                  10                  15

Gly Val Phe Lys Tyr Val Leu Ile Arg Val His Leu Ala Glu Pro Ser
                20                  25                  30

Gly Asp Pro Ala Lys Glu Cys Lys Glu Ile Val Arg Gly Tyr Lys Trp
                35                  40                  45
```

```
Ala Glu Tyr His Ala Asp Ile Tyr Asp Lys Val Ser Gly Glu Leu Gln
     50                  55                  60

Arg Asn Gly Tyr Asp Cys Glu Cys Leu Gly Gly Gly Arg Ile Ser His
 65                  70                  75                  80

Gln Ser Gln Asp Arg Lys Ile His Val Tyr Gly Tyr Ser Met Gly Tyr
                 85                  90                  95

Gly Arg Ala Gln His Ser Val Ser Thr Glu Lys Ile Lys Ala Lys Tyr
            100                 105                 110

Pro Asp Tyr Glu Val Thr Trp Ala Asp Asp Gly Tyr
        115                 120

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Peptide for
      generating an  antibody directed against histidine
      protein phosphatase

<400> SEQUENCE: 9

Gln Ile Pro Asp Val Asp Ile Asp Ser Asp Gly Val Phe Lys Tyr Val
  1               5                  10                  15

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: peptide for
      generating an antibody directed against histidine
      protein phosphatase

<400> SEQUENCE: 10

Cys Leu Gly Gly Gly Arg Ile Ser His Gln Ser Gln Asp Lys
  1               5                  10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: peptide for
      generating an antibody directed against histidine
      protein phosphatase

<400> SEQUENCE: 11

Cys Thr Glu Lys Ile Lys Ala Lys Tyr Pro Asp Tyr Glu Val
  1               5                  10
```

What is claimed is:

1. An isolated mammalian polypeptide having the enzyme activity of a histidine protein phosphatase which specifically dephosphorylates phosphohistidine and has a molecular weight of 13,000–15,000 Da as determined by SDS electrophoresis, and which is isolated by a method comprising at least one step of anion exchange chromatography, gel filtration and Blue sepharose affinity chromotogaphy.

2. An isolated polypeptide according to claim 1 comprising at least the amino acid sequence motif
DCECLGGGRISHQSQD (SEQ ID NO:3).

3. An isolated polypeptide according to claim 1 comprising at least the amino acid sequence motif
DCECLGGGRISHQSQDX$^1$KIHVYGYSMX$^2$YGX$^3$AQH (SEQ ID NO:4)
wherein X$^1$=K or R, X$^2$=A or G and X$^3$=P or R.

4. An isolated polypeptide according to claim 1 comprising at least the amino acid sequence motif
YHADIYDKVSGDMQKQGCDCECLGGGR-ISHQSQDKKIHVYGYSM (SEQ ID NO:5).

5. An isolated mammalian polypeptide having the enzyme activity of a histidine protein phosphatase which specifically dephosphorylates phosphohistidine and has a molecular weight of 13,000–15,000 Da as determined by SDS electrophoresis, comprising the SEQ ID NO:2.

6. A composition comprising a polypeptide according to claim 1 and, a pharmaceutically suitable excipients, carriers, and other active ingredients.

7. An antibody directed to a polypeptide according to claim 1.

8. A method of producing a recombinant human histidine protein phosphatase, comprising:
   expressing a cDNA coding for a human histidine protein phosphatase having the amino acid sequence of SEQ ID NO 2 in a cell to produce recombinant human histidine protein phosphatase, and
   isolating said recombinant human histidine protein phosphatase.

9. A method of claim 8, where said cDNA comprises the nucleotide sequence of SEQ ID NO:1.

* * * * *

UNITED STATES PATENT AND TRADEMARK OFFICE
CERTIFICATE OF CORRECTION

PATENT NO. : 6,812,015 B1
DATED : November 2, 2004
INVENTOR(S) : Klumpp et al.

It is certified that error appears in the above-identified patent and that said Letters Patent is hereby corrected as shown below:

Column 17,
Line 8, change "chromotogaphy" to -- chromotography --.

Signed and Sealed this

Twelfth Day of April, 2005

JON W. DUDAS
*Director of the United States Patent and Trademark Office*